United States Patent
Beeckler et al.

(10) Patent No.: US 12,268,509 B2
(45) Date of Patent: Apr. 8, 2025

(54) FLEXIBLE CIRCUIT WITH LOCATION AND FORCE-SENSOR COILS

(71) Applicant: BIOSENSE WEBSTER (ISRAEL) LTD., Yokneam (IL)

(72) Inventors: Christopher T. Beeckler, Brea, CA (US); Joseph T. Keyes, Sierra Madre, CA (US); Kevin J. Herrera, West Covina, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 18/301,829

(22) Filed: Apr. 17, 2023

(65) Prior Publication Data

US 2023/0293080 A1 Sep. 21, 2023

Related U.S. Application Data

(62) Division of application No. 16/036,710, filed on Jul. 16, 2018, now Pat. No. 11,672,461.

(51) Int. Cl.
| | |
|---|---|
| *A61B 5/00* | (2006.01) |
| *A61B 5/0538* | (2021.01) |
| *A61B 5/06* | (2006.01) |
| *A61B 5/282* | (2021.01) |
| *A61B 5/341* | (2021.01) |

(52) U.S. Cl.
CPC ............ *A61B 5/341* (2021.01); *A61B 5/0538* (2013.01); *A61B 5/063* (2013.01); *A61B 5/282* (2021.01)

(58) Field of Classification Search
CPC ...... A61B 18/1492; A61B 2018/00357; A61B 2018/00577; A61B 2018/00839; A61B 2090/065; A61B 5/0538; A61B 5/063; A61B 5/282; A61B 5/341; G01L 1/042; G01L 1/14

See application file for complete search history.

(56) References Cited

U.S. PATENT DOCUMENTS

| | | | |
|---|---|---|---|
| 6,171,275 B1 | 1/2001 | Webster, Jr. | |
| 6,226,542 B1 | 5/2001 | Reisfeld | |
| 6,241,724 B1 | 6/2001 | Fleischman et al. | |

(Continued)

FOREIGN PATENT DOCUMENTS

| | | |
|---|---|---|
| CN | 1906471 A | 1/2007 |
| CN | 103908337 A | 7/2014 |

(Continued)

OTHER PUBLICATIONS

Ataollahi, A., et al., "Novel Force Sensing Approach Employing Prismatic-tip Optical Fiber Inside an Orthoplanar Spring Structure," IEEE/ASME Transactions on Mechatronics, vol. 19, No. 1, Feb. 2014, pp. 121-130.

(Continued)

*Primary Examiner* — Mark D Remaly
(74) *Attorney, Agent, or Firm* — Etan S. Chatlynne; Calderon Safran & Wright P.C.

(57) ABSTRACT

A flexible circuit that is substantially planar may be assembled into an electrophysiologic catheter. The flexible circuit may include various location sensing portions and force sensing portions. The flexible circuit may be deformed in a manner that improves the catheter's functionality concerning force feedback and location feedback, and then further deformed to be assembled into a small volume of the catheter.

14 Claims, 8 Drawing Sheets

(56) References Cited

U.S. PATENT DOCUMENTS

| | | |
|---|---|---|
| 6,253,770 B1 | 7/2001 | Acker et al. |
| 6,301,496 B1 | 10/2001 | Reisfeld |
| 6,695,808 B2 | 2/2004 | Tom |
| 6,814,733 B2 | 11/2004 | Schwartz et al. |
| 6,892,091 B1 | 5/2005 | Ben-Haim et al. |
| 6,915,149 B2 | 7/2005 | Ben-Haim |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 9,204,820 B2 | 12/2015 | Clark et al. |
| 2005/0267332 A1 | 12/2005 | Paul et al. |
| 2007/0100332 A1 | 5/2007 | Paul et al. |
| 2007/0214897 A1 | 9/2007 | Ogawa |
| 2009/0093806 A1 | 4/2009 | Govari et al. |
| 2009/0099551 A1 | 4/2009 | Tung et al. |
| 2011/0130648 A1 | 6/2011 | Beeckler et al. |
| 2013/0102868 A1 | 4/2013 | Fandrey et al. |
| 2014/0018665 A1 | 1/2014 | Meredith |
| 2014/0187917 A1 | 7/2014 | Clark et al. |
| 2014/0276006 A1 | 9/2014 | Sliwa et al. |
| 2014/0378968 A1 | 12/2014 | Sutermeister et al. |
| 2015/0105773 A1 | 4/2015 | Weber et al. |
| 2016/0228180 A1 | 8/2016 | Sliwa et al. |
| 2017/0027476 A1 | 2/2017 | Kariv |
| 2017/0055873 A1 | 3/2017 | Clark et al. |
| 2017/0172666 A1 | 6/2017 | Govari et al. |
| 2017/0194384 A1 | 7/2017 | Zhou et al. |
| 2017/0354467 A1 | 12/2017 | Rankin et al. |
| 2018/0125382 A1 | 5/2018 | Govari et al. |

FOREIGN PATENT DOCUMENTS

| | | |
|---|---|---|
| CN | 205041520 U | 2/2016 |
| CN | 105496548 A | 4/2016 |
| CN | 105581840 A | 5/2016 |
| CN | 106371672 A | 2/2017 |
| CN | 107028653 A | 8/2017 |
| EP | 3167835 A1 | 5/2017 |
| JP | 2002082006 A | 3/2002 |
| JP | 2002238844 A | 8/2002 |
| JP | 2008525120 A | 7/2008 |
| JP | 2011149861 A | 8/2011 |
| JP | 2014128676 A | 7/2014 |
| JP | 2014128680 A | 7/2014 |
| JP | 2016536065 A | 11/2016 |
| WO | 9605768 A1 | 2/1996 |

OTHER PUBLICATIONS

Extended European Search Report for European Application No. 18160424, mailed on Jun. 28, 2018, 7 pages.

Extended European Search Report for European Application No. EP19186215, mailed on Jan. 21, 2020, 6 pages.

Search Report from corresponding Japanese Patent Application No. 2018040493, dated Oct. 15, 2021, 18 pages.

FLEXIBLE CIRCUIT WITH LOCATION AND FORCE-SENSOR COILS

CROSS-REFERENCE TO CO-PENDING APPLICATION

This application is a Divisional Application under 35 U.S.C. § 121 of U.S. patent application Ser. No. 16/036,710, filed Jul. 16, 2018. This application is also related to U.S. patent application Ser. No. 15/452,843, filed Mar. 8, 2017, now U.S. Pat. No. 11,317,965, issued on May 3, 2022. The entire contents of these applications are incorporated by reference herein in their entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD

The subject matter disclosed herein relates to instruments for diagnostic and surgical purposes that measure force, pressure or mechanical tension or compression using catheters for diagnostic and surgical procedures in the heart.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

SUMMARY OF THE DISCLOSURE

Improvements to patient outcomes for therapies involving ablation of tissues, particularly to cardiac tissues, are being pursued. The subject matter disclosed herein concerns structures within an electrophysiologic catheter that may be used to provide feedback to a user of that catheter concerning, e.g., location of the catheter and force exerted on the catheter tip. Applicant has overcome various design constraints to provide a catheter having, among other things, a flexible circuit that is capable of providing the feedback in a safe and effective manner.

Disclosed herein is a flexible circuit. The flexible circuit may comprise a substantially planar substrate including a first portion of a first shape (e.g., circular) and a second portion of a second shape that is different from the first shape (e.g., rectangular or substantially rectangular). A first substantially planar force-sensing coil my be disposed on the first portion and a first substantially planar location coil may be disposed on the second portion. Further, the second portion may include a first segment connected to a second segment by a first connector segment such that the first substantially planar location coil may be disposed on the first segment. In such embodiments, a second substantially planar location coil may also disposed on the second segment such that, preferably, the first segment and first substantially planar location coil forms a generally mirror image of the second segment and second substantially planar location coil. Accordingly, the first substantially planar location coil may have a clockwise orientation and the second substantially planar location coil may have a counterclockwise orientation. Alternatively, the first substantially planar location coil may have a counterclockwise orientation and the second substantially planar location coil may have a clockwise orientation.

In further embodiments, the substantially planar substrate may further comprise a third portion including a third segment connected to a fourth segment by a second connector segment. A third substantially planar location coil may be disposed on the third segment and a fourth substantially planar location coil may be disposed on the forth segment. Similar to the first and second segments, the third segment and third substantially planar location coil mirror the fourth segment and fourth substantially planar location coil.

In further embodiments, the substantially planar substrate may include a fourth portion connected to and disposed between the first portion, the second portion, and the third portion, e.g., by a third connector segment, a fourth connector segment, and a fifth connector segment, respectively.

Additional connector segments may further be provided. For example, the substantially planar substrate may also include a sixth connector segment connecting the first segment to the second segment and a seventh connector segment connecting the third segment to the fourth segment.

The various coils described above may be connected to solder joints disposed on the fourth portion. For example, a portion of the second substantially planar location coil may extend from the second segment of the second portion to a first solder joint on the fourth portion via the first connector segment and the first segment of the second portion. Also, an extension of the force-sensing coil may extend to a second solder joint on the fourth portion.

As noted, the first portion may have a circular shape. The circular shape may comprise a trefoil shape having a fifth segment upon which is disposed the first substantially planar force-sensing coil, a sixth segment upon which is disposed a second substantially planar force-sensing coil, and a seventh segment upon which is disposed a third substantially planar force-sensing coil.

In any embodiment, the substrate may be fabricated by a lithographic process. The substantially planar substrate may include between two layers and ten layers, for example four layers. Further, additional material (e.g., polyimide) may be disposed on at least one of the second portion, the third portion, and the fourth portion.

The flexible circuit, in any embodiment, is, as its name suggests, flexible. Further, it is dimensioned such that a deformation of the second connector and the third connector reduces a distance between the second portion and third portion to be approximately equal to a maximum width of the first portion. The deformation of the second connector and the deformation of the third connector may be circular deformations. Further, deformation of the fourth connector may cause the second segment to contact and overlap the first segment, and deformation of the fifth connector may cause the fourth segment to contact and generally overlap the third segment. Additionally, deformation of the third connector may align the second substantially planar location coil with the first substantially planar location coil and deformation of the fourth connector may align the fourth substantially planar location coil with the third substantially planar location coil.

The flexible circuit may be assembled into a catheter according to the following method and variations. First, the first portion may be oriented to be parallel to a face of a spring oriented transversely to a longitudinal axis of the spring. Then the first portion may be affixed to the face of the spring. Second, the second portion and third portion may be oriented to be parallel, respectively, to two outer portions of a coupling sleeve. Then the second portion and the third portion may be respectively connected to the two outer surface portions. Third, the coupling sleeve may be coupled to an outer sleeve. Fourth, the spring may be coupled to a catheter tip. In some variations, the face of the spring may be oriented relative to the longitudinal axis of the spring at an angle of greater than about sixty degrees and less than ninety degrees. Typically, the spring may be fabricated with such attributes prior to assembly. For example, the angle may be about eighty degrees.

Fifth, a gap may be filled between the outer sleeve and at least one of the second portion, the third portion, and the fourth portion. The step of filling the gap includes providing the additional material (e.g., polyimide) on the at least one of the second portion, the third portion, and the fourth portion. The additional material may be provided onto the at least one of the second portion, the third portion, and the fourth portion either before or after the coupling sleeve is coupled to the outer sleeve.

As used herein, the terms "substantially planar" and "generally planar" should be understood as indicating a planar configuration of an object or an approximately planar configuration of that object that would be acceptable to one skilled in the art for an intended use of the object.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

The subject matter disclosed herein concerns structures within the catheter that may be used to provide feedback to a user of an ablation catheter (e.g., electrophysiologist), the feedback concerning catheter location and the force exerted on the catheter's tip and any electrodes disposed thereon. These structures must fit within the small inner diameter of the catheter (e.g., often equal to or less than about 0.1 inch) yet overcome various design constraints related thereto to provide the feedback reliably. For example, metal coils may be used to detect location within a magnetic field. Generally, larger and thicker coils with more turns are easier to detect than smaller and thinner coils with fewer turns; however, due to the small space within the catheter, the coils must be small and thin to fit therein. Further, when such coils are fabricated as traces on a circuit board or flexible circuit via a lithographic process, the process limits the trace pitch. Although the option is available to increase thickness of the circuit by additional layers lithographically, this option has two disadvantages. First, it is expensive because fabrication costs are proportional to the number of layers. That is, other things being equal, a flexible circuit having more layers costs more to fabricate than one having fewer layers. Second, non-linearity of yield is also proportional to the number of layers. That is, the yield from the coils is compromised because non-linearity of the yield increases with the number of traces. These design challenges are compounded by inclusion of additional structures proximate to the location traces, including irrigation structures and a force measurement assembly that must be capable of reliably providing sub-gram force measurements. Further, cross-talk interference that may arise from packing the structures in a tight space should be accounted for. So too should the need for ease of assembly and wiring for safe products and positive patient outcomes.

Figure 1:
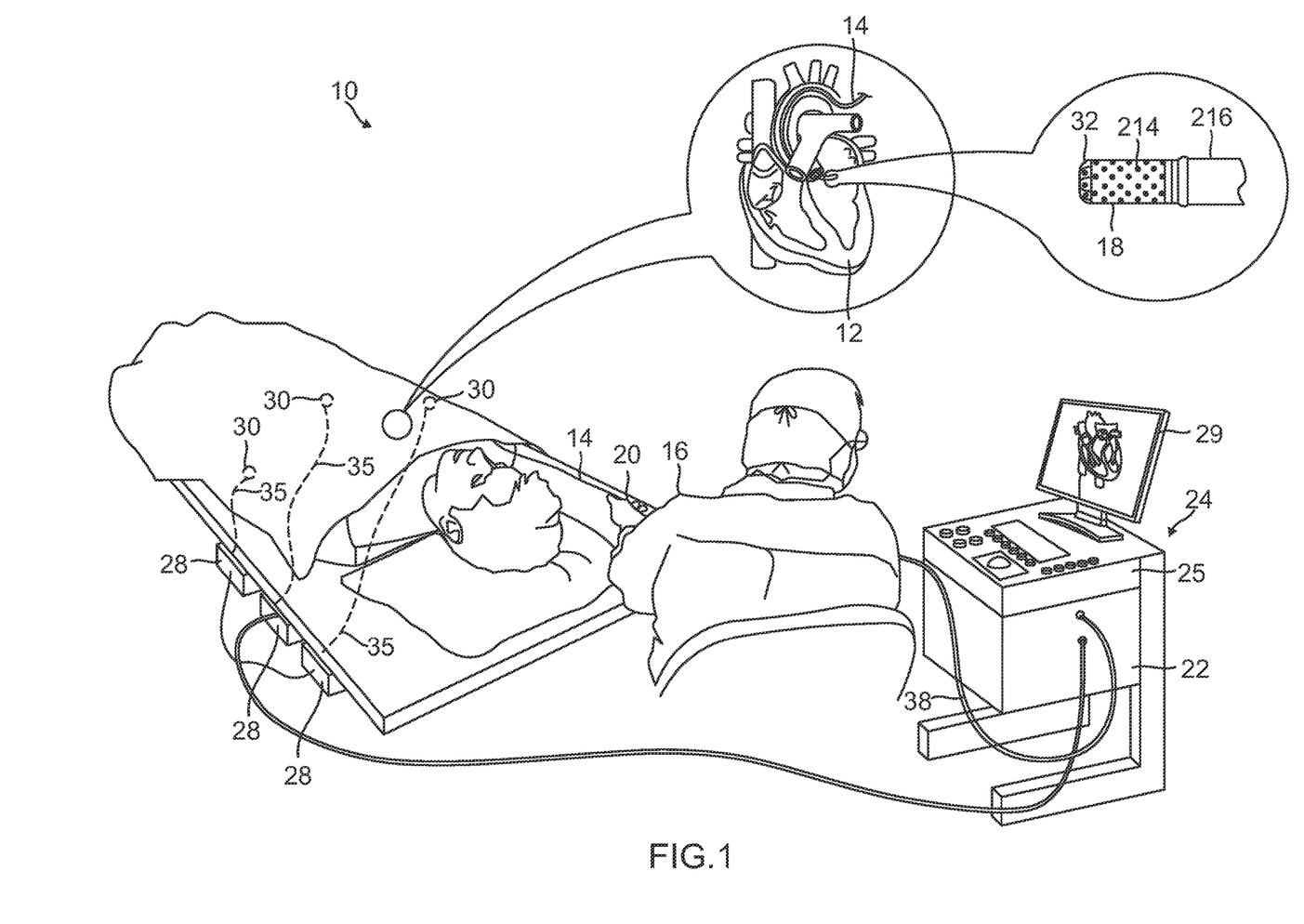
FIG. 1 is a pictorial illustration of a system for evaluating electrical activity in a heart of a living subject and providing treatment thereto using a catheter.

FIG. 1 is a pictorial illustration of a system 10 for evaluating electrical activity and performing ablative procedures on a heart 12 of a living subject. The system includes a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S.

Pat. No. 6,892,091, whose disclosures are herein incorporated by reference in their entirety. One commercial product embodying elements of system 10 is available as the CARTO® 3 System, available from Biosense Webster, Inc., 33 Technology Drive, Irvine, CA, 92618.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to target tissue. The energy is absorbed in the tissue, heating it to a point (typically above 50° C.) at which point it permanently loses its electrical excitability. This procedure creates non-conducting lesions in the cardiac tissue, which disrupt the abnormal electrical pathway causing the arrhythmia. Such principles can be applied to different heart chambers to diagnose and treat many different types of cardiac arrhythmias.

The catheter 14 typically includes a handle 20, having suitable controls on the handle to enable the operator 16 to steer, position and orient the distal end of the catheter as desired for the ablation. To aid the operator 16, distal portion 18 of catheter 14, or portions proximate thereto, contains position sensors, e.g., traces or coils (discussed below), that provide signals to a processor 22, located in a console 24.

Ablation energy and electrical signals can be conveyed to and from the heart 12 through one or more ablation electrodes 32 located at or near the distal tip 18 via cable 38 to the console 24. Pacing signals and other control signals may be conveyed from the console 24 through the cable 38 and the electrodes 32 to the heart 12.

Wire connections 35 link the console 24 with body surface electrodes 30 and other components of a positioning sub-system for measuring location and orientation coordinates of the catheter 14. The processor 22 or another processor may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference in its entirety. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, cryogenic energy, and laser-produced light energy. Such methods are disclosed in commonly assigned U.S. Pat. Nos. 6,814,733, 6,997,924, and 7,156,816, which are herein incorporated by reference in their entirety.

The positioning subsystem may also include a magnetic position tracking arrangement that determines the position and orientation of the catheter 14 by generating magnetic fields in a predefined working volume and sensing these fields at the catheter, using coils or traces disposed within the catheter, typically proximate to the tip. A positioning sub-system is described in U.S. Pat. No. 7,756,576, which is hereby incorporated by reference in its entirety, and in the above-noted U.S. Pat. No. 7,536,218.

Operator 16 may observe and regulate the functions of the catheter 14 via console 24. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing coils or traces located distally in the catheter 14. The digitized signals are received and used by the console 24 and the positioning system to compute the position and orientation of the catheter 14, and to analyze the electrical signals from the electrodes and the contact force sensors.

The subject matter disclosed herein concerns structures within the catheter that may be used to provide feedback to operator 16. Specifically, this feedback concerns the location of the catheter and its tip as well as the force exerted on the catheter's tip and any electrodes disposed thereon. These structures must fit within the small inner diameter of the catheter (e.g., often equal to or less than about 0.1 inch) yet overcome various design constraints related thereto to provide the feedback reliably. For example, metal coils may be used to detect location within a magnetic field. Generally, larger and thicker coils are easier to detect than smaller and thinner coils, however, due to the small space within the catheter, the coils must be small and thin to fit therein. Further, when such coils are fabricated as traces on a circuit board or flexible circuit via a lithographic process, the process limits the trace pitch. Although the option is available to increase thickness of the traces by additional layers lithographically, this option has two disadvantages. First, it is expensive because more layers cost more than fewer layers. Second, the yield from the coils is compromised insofar as non-linearity of the yield increases with the number of traces. These design challenges are compounded by inclusion of additional structures proximate to the location traces that must be capable of reliably providing sub-gram force measurements and that lack cross-talk interference that may arise from packing the structures in a tight space, as well as the need for ease of assembly and wiring for safe products and positive patient outcomes.

Figure 2:
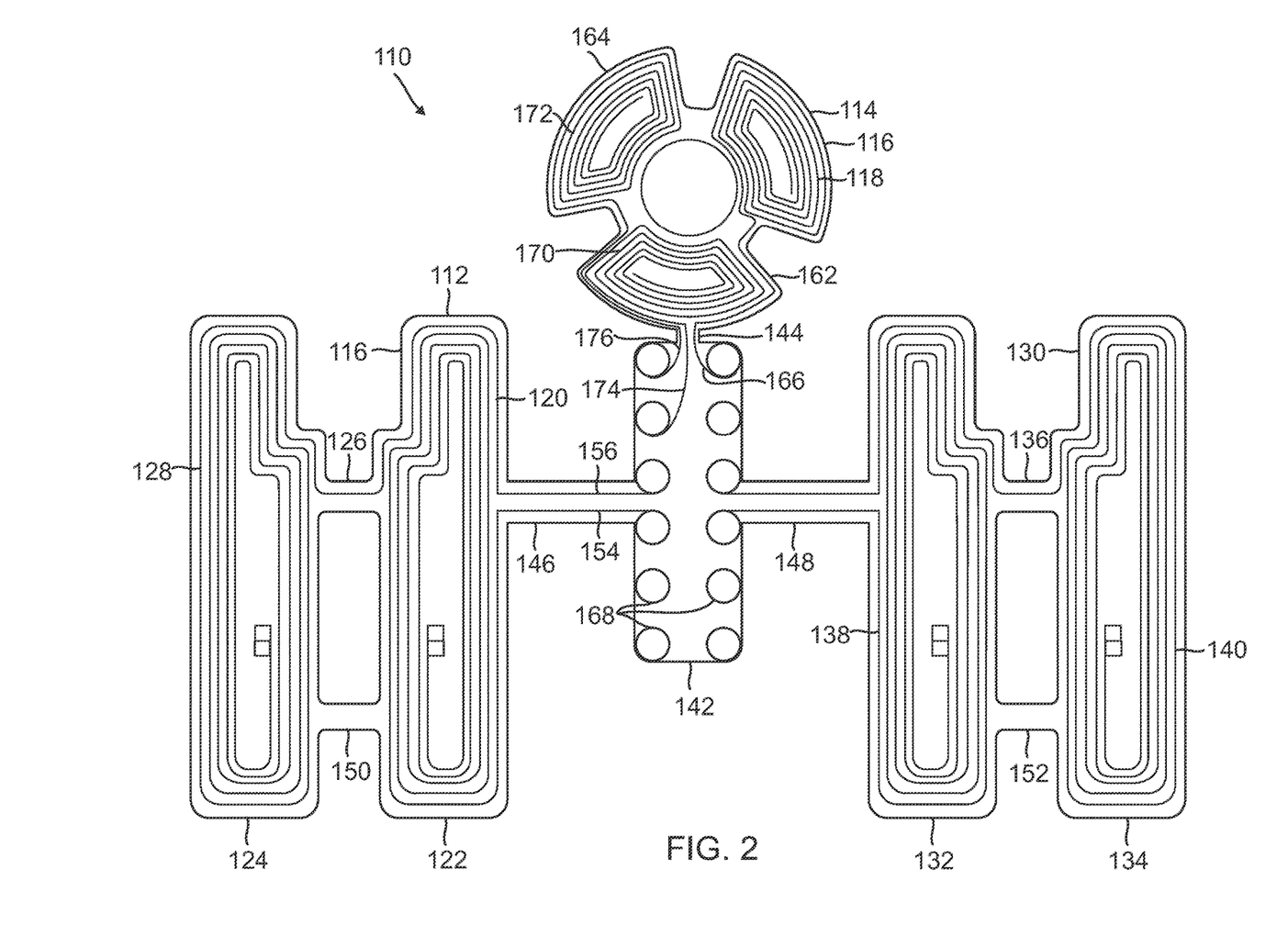
FIG. 2 depicts a flexible-circuit component of the catheter of FIG. 1.

FIG. 2 reflects a flexible circuit 110 that may be employed within a catheter, such as catheter 14, to provide signals concerning location and force to a processor in console 24. Flexible circuit 110 includes a substantially planar substrate 112 having a first portion 114 of a first shape (e.g., circular or trefoiled as shown) and a second portion 116 of a second shape (e.g., substantially rectangular or polygonal as shown). First portion 114 and second portion 116 are typically of different shapes because, as will be explained below, second portion 116 is assembled parallel to the longitudinal axis of the catheter, such that it should be elongate, whereas first portion 114 is assembled transversely to the longitudinal axis of the catheter, such that it should conform to the inner diameter of the catheter (i.e., have a maximum width or diameter that is less than or about equal to the inner diameter of the catheter). Nonetheless, shapes of first portion 114 and second portion 116 may be similar. Substrate may be formed of any suitable material that is non-conductive and is capable of resisting high temperatures, e.g., polyimide, polyamide, or liquid crystal polymer (LCP).

Substrate 112 may also include additional portions, such as third portion 130 and fourth portion 142. Each of these portions may further include various segments. As noted, first portion 114 may be of a trefoil shape. Thus, it may have three segments, i.e., segments 160, 162, and 164. Second portion 116 may include segment 122 and segment 124, and at least one connector segment, such as 126 or 150, which connect segment 122 to segment 124. Third portion 130 may have a similar structure to second portion 116, and may include segment 132 and segment 134, and at least one connector segment, such as 136 or 152, which connect segment 132 to segment 134. Fourth portion 142 may include at least three connector segments 144, 146 and 148, which connect fourth portion 142 to first, second, and third portions 114, 116, and 130.

Electrical components may be incorporated into substrate 112 and its various portions and segments. For example, substantially planar coils or traces used to measure signals relating to force (i.e., force-sensing coils or traces) may be incorporated onto first portion 114. Specifically, coil 118 may incorporated with segment 160, coil 170 may be incorporated with segment 162, and coil 172 may be incorporated with segment 164. Coils 118, 170, and 172 may be discrete from each other, as shown, or they may each be connected to one or both of the others. Portions of each coil, or extensions thereof, may extend from the coil to solder joints 168 located on fourth portion 142 and be soldered thereto. Where the three coils are discrete from each other, each should include a respective extension (i.e., 166, 174, and 176). However, where the three coils are connected, only one or two extensions may be necessary. Where the coils are discrete from each other, the signals generated in each of the coils may be used to provide additional details of force, such as an indication of an off-center force or an off-axis direction of the force. As shown, each coil on first portion 114 includes approximately five turns. However, because signal strength is a function of the number of turns, the number of turns may be maximized based on the size of each segment and the pitch that the lithographic process can accomplish.

Planar coils or traces used to measure signals relating to location (i.e., location coils or traces) may also be incorporated into second portion 116 and third portion 130. Coil 120 may be incorporated with segment 122, coil 128 may be incorporated with segment 124, coil 138 may be incorporated with segment 132, and coil 140 may be incorporated with segment 134. Each of these coils may extend to solder joints 168 on fourth portion 142. For example, coil 120 may include an extension 154 that connects to a solder joint 168 via connector segment 146 and coil 128 may include an extension 156 that connects to a solder joint 168 via connector segment 126, segment 122 and connector segment 146. As shown, each coil on first and second portions 116 and 130 includes approximately five turns. However, because signal strength is a function of the number of turns, the number of turns may be maximized based on the size of segments 122, 124, 132, and 134, and the pitch that the lithographic process can accomplish.

Various symmetries are reflected in FIG. 2. For example, the entire substrate is symmetric about a midline passing through the center of first portion 114, such that second portion 116 is laterally disposed to one side of first portion 114 and fourth portion 142 and such that third portion 130 is laterally disposed to the other side of first portion 114 and fourth portion 142. Thus, fourth portion 142 is disposed between first portion 114, second portion 116 and third portion 130. Further, segments 122 and 124 mirror each other, and, with the exception of extension 156, coil 120 mirrors coil 128. The same is true for segments 132 and 134, as well as coils 138 and 140. Accordingly, and as shown, the wind of coils 120 and 132 may be clockwise (i.e., have a clockwise orientation) whereas the wind of coils 128 and 134 may be counterclockwise (i.e., have a counterclockwise orientation). Alternatively, the wind of coils 120 and 132 may be counterclockwise and the wind of coils 128 and 134 may be clockwise.

Substrate 112 may be a single layer. Alternatively, it may include between two and ten layers, e.g., four layers. In this manner the coils may be thickened by adding layers. However, as described above, thickening by layers results in increased non-linearity of signal yield. The flexibility of flexible circuit 110 enables a solution to this tradeoff. Specifically, referring to FIG. 3, by deforming or bending connector 126 and connector 150, segment 124 may be folded on top of segment 122 to contact it and overlap it such that coil 128 aligns with coil 120. Similarly, by deforming or bending connector 136 and connector 152, segment 134 may be folded on top of segment 132 to contact it and overlap it such that coil 140 aligns with coil 138. Although connectors 150 and 152 are optional, they may assist aligning the coils with each other by reducing relative rotation between the segments. If substrate 112 is four layers, for example, then after segment 124 is folded onto segment 122, coils 120 and 128 form a combined coil having eight layers. Although panelization density due to increased area may increase, the yield of the combined coil does not suffer from increased non-linearity as would the eight-layer coil fabricated in an eight-layer substrate.

Figure 3:
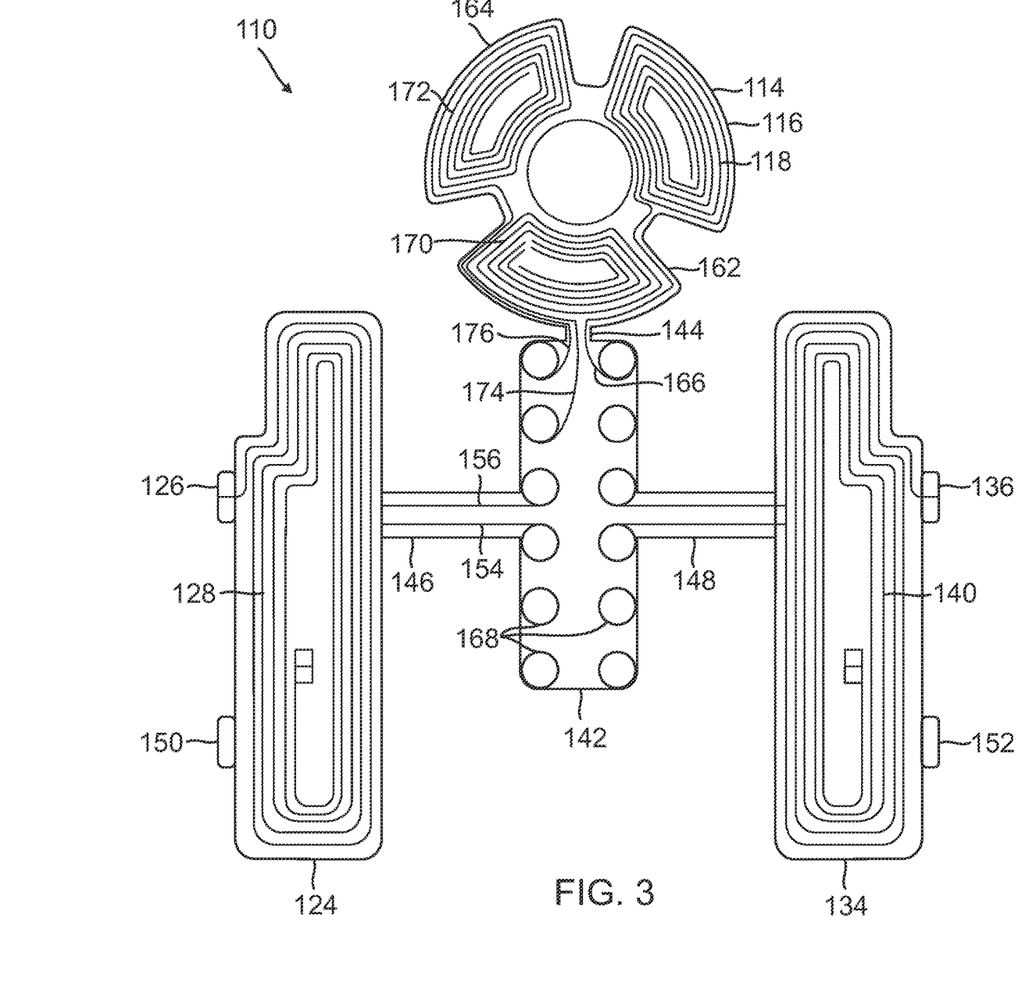
FIG. 3 depicts the flexible-circuit component of FIG. 2 in a modified configuration.

An advantage that a thinner substrate (e.g., four layers) has over a thicker substrate (e.g., eight layers) is that it is easier to deform or bend, which is helpful for assembling flexible circuit 110 to other catheter components and ultimately for fitting it within the inner-diameter envelope of the catheter, as will be detailed below. Accordingly, flexible circuit 110 allows for a thick coil without increased non-linearity of the signal and increased stiffness of the substrate.

Figure 4:
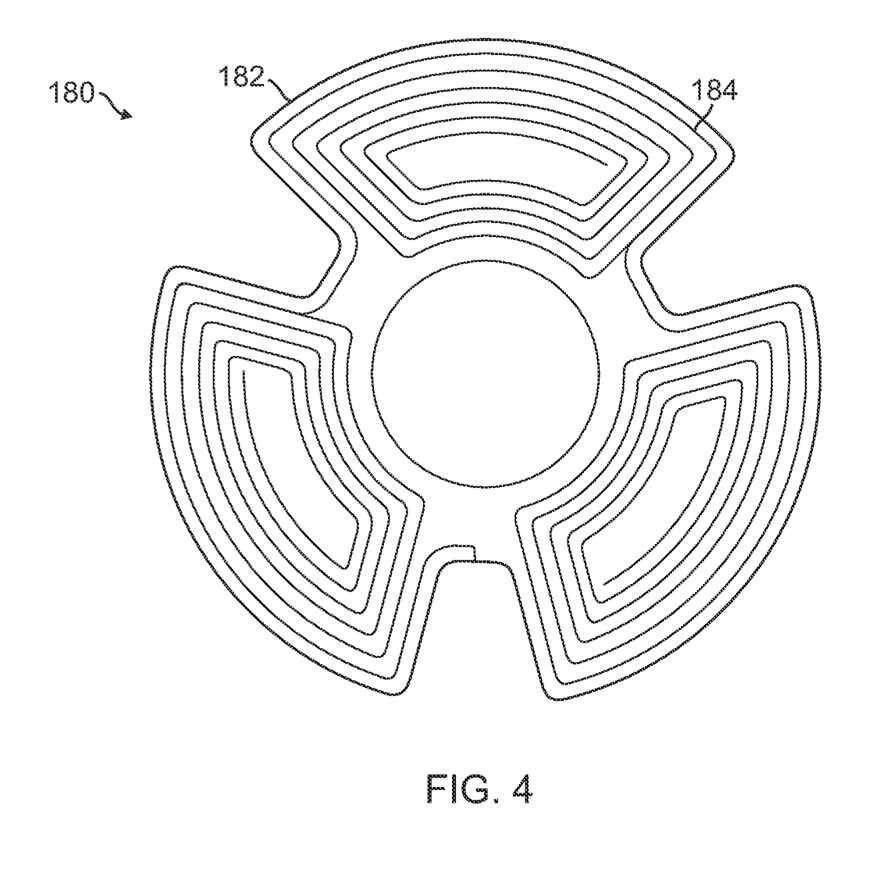
FIG. 4 depicts another flexible-circuit component of the catheter of FIG. 1.

FIG. 4 reflects another component of catheter 14, flexible circuit 180, which includes substrate 182 and coil or coils 184. The structure of flexible circuit 180 is similar to the structure of first portion 114 of flexible circuit 110. However, in various embodiments, the number or pitch of the coils may vary, and the various coils on the three segments may be discrete from each other or integrated with each other.

Figure 5:
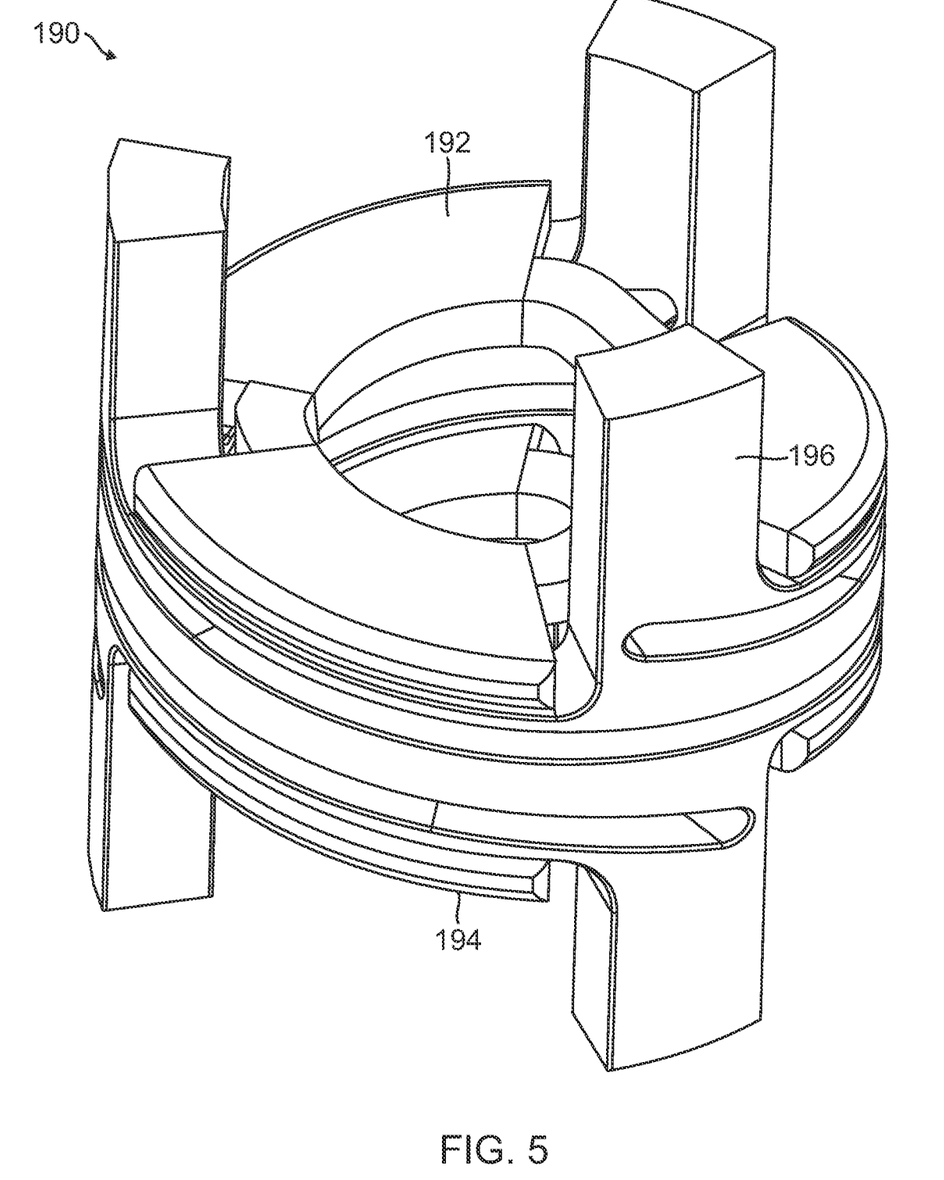
FIG. 5 depicts a spring component of the catheter of FIG. 1.

FIG. 5 reflects another component of catheter 14, helical spring 190, that includes a top face 192, a bottom face 194, and various arms 196 that may be used to assemble spring 190 to other components of catheter 14. Spring 190 has a known or predetermined spring constant that relates distance to force in accordance with Hooke's law. Together flexible circuit 180, first portion 114 of flexible circuit 110, and helical spring 190 make up a sub-assembly that may receive electrical signals from and provide electrical signals to console 24, which may be processed to determine forces, e.g., sub-gram forces, exerted on tip 18 of catheter 14. Specifically, a first cable or cables (within cable-bundle 198 of FIGS. 6 and 7) that connects to console 24 on one end may be also connected at the opposite end to solder joints 168 of fourth portion 142 of flexible circuit 110 that are connected via coil extensions 166, 174, and 176 to coils 118, 170, and 172 on segments 160, 162, and 164 of first portion 114, respectively. A second cable or cables (also within cable-bundle 198) that connects to console 24 on one end may also be connected at the opposite end to coil or coils 184 on flexible circuit 180. Electrical signals from console 24, e.g., having RF frequencies, may be used to power either the coils on the first portion of flexible circuit 110 or the coils on flexible circuit 180. Whichever set of coils receives power from console 24 may be considered a transmitter because it emits an electromagnetic field that varies in accordance with the frequency of the signals received from console 24. The set of coils that is not powered by console 24 may be considered a receiver in as much as it functions like an antenna in response to the electromagnetic field from the transmitter. Thus the receiver generates electrical signals that may be conveyed to console 24 for analysis. The electrical signals generated by the receiver depend on the distance between the receiver and the transmitter, such that the electrical signals generated by the receiver may be correlated to the distance between the receiver and the transmitter.

By adhering the receiver (here, the coils on first portion 114 of flexible circuit 110) to top face 192 of spring 190 and the transmitter (here, the coils on flexible circuit 180) to the bottom face of spring 180, and wiring them as described above, electrical signals generated in the receiver may be correlated to compression displacement in the spring (e.g., on the order of 100 nanometers) and thus to forces against tip 18 of catheter 14 that cause spring 180 to compress. In use, console 24 may process these signals and use them to regulate the amount of ablation energy supplied to electrodes. For example, when the signals indicate that the spring is in a relaxed state (i.e., no compression) this may be perceived as an indicator that tip 18 of catheter 14 does not contact tissue, and therefore, no ablation energy should be supplied to the electrodes. Indicators of the information (e.g., in units of force, such as newtons) may further be provided to operator 16 on monitor 29. This information may be useful to provide directly to operator 16 insofar as it may help operator 16 avoid damaging tissue by pressing tip 18 against it too hard.

Top face 192 and bottom face 194 of spring 190 may be parallel to each other and oriented transversely to the longitudinal axis of the spring (e.g., at an angle of greater than about sixty degrees and less than ninety degrees, e.g., about eighty degrees). Accordingly, the receiver and the transmitter, affixed thereto, are similarly angulated. The inventors have determined that transverse but nonperpendicular angulation increases the sensitivity of the receiver because the distance between the transmitter and receiver is minimized as compared to if they were provided perpendicular to the spring's longitudinal axis, and ultimately the catheter's longitudinal axis.

Figure 6:
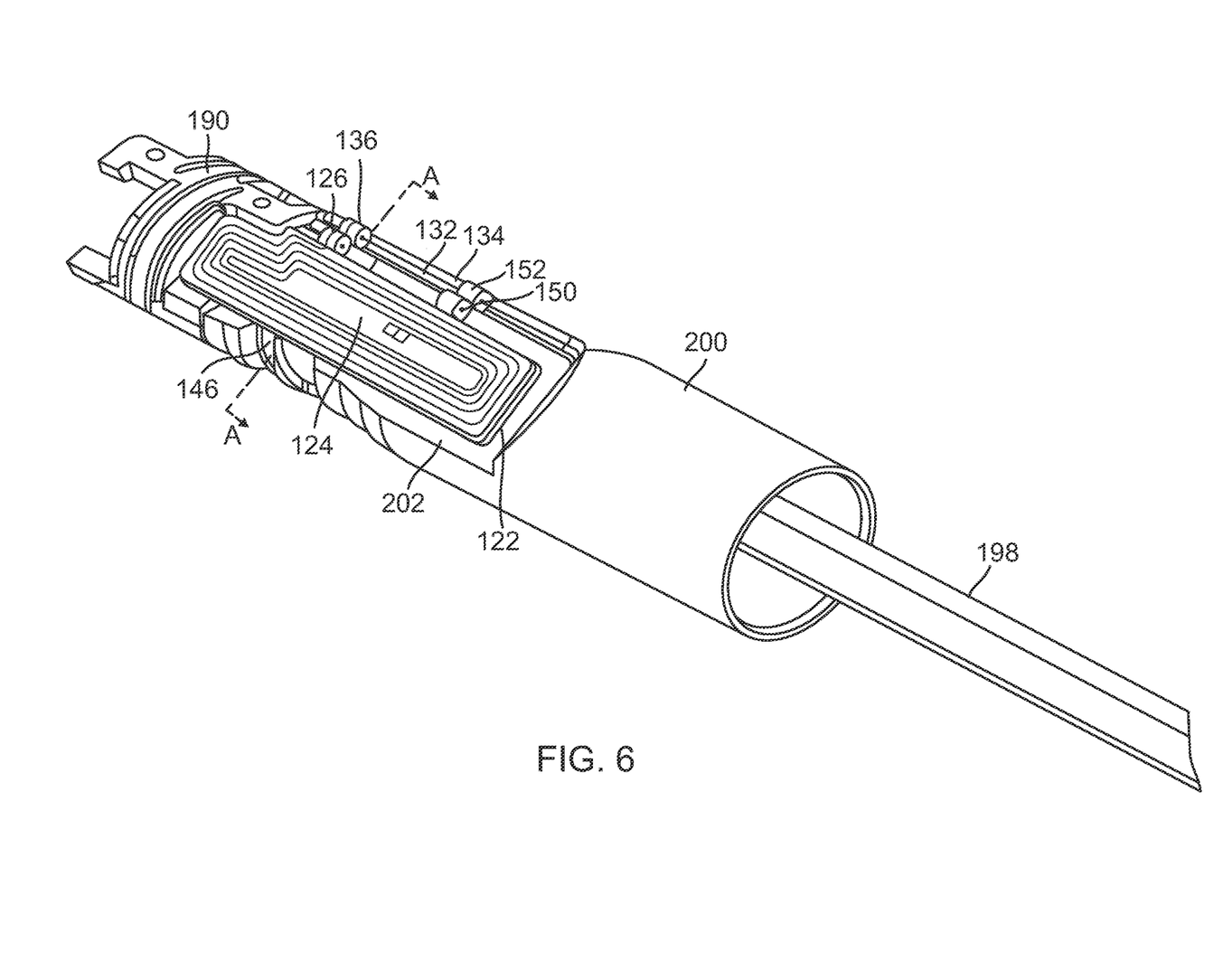
FIG. 6 depicts a distal portion of the catheter of FIG. 1 in a partially assembled configuration.
Figure 7:
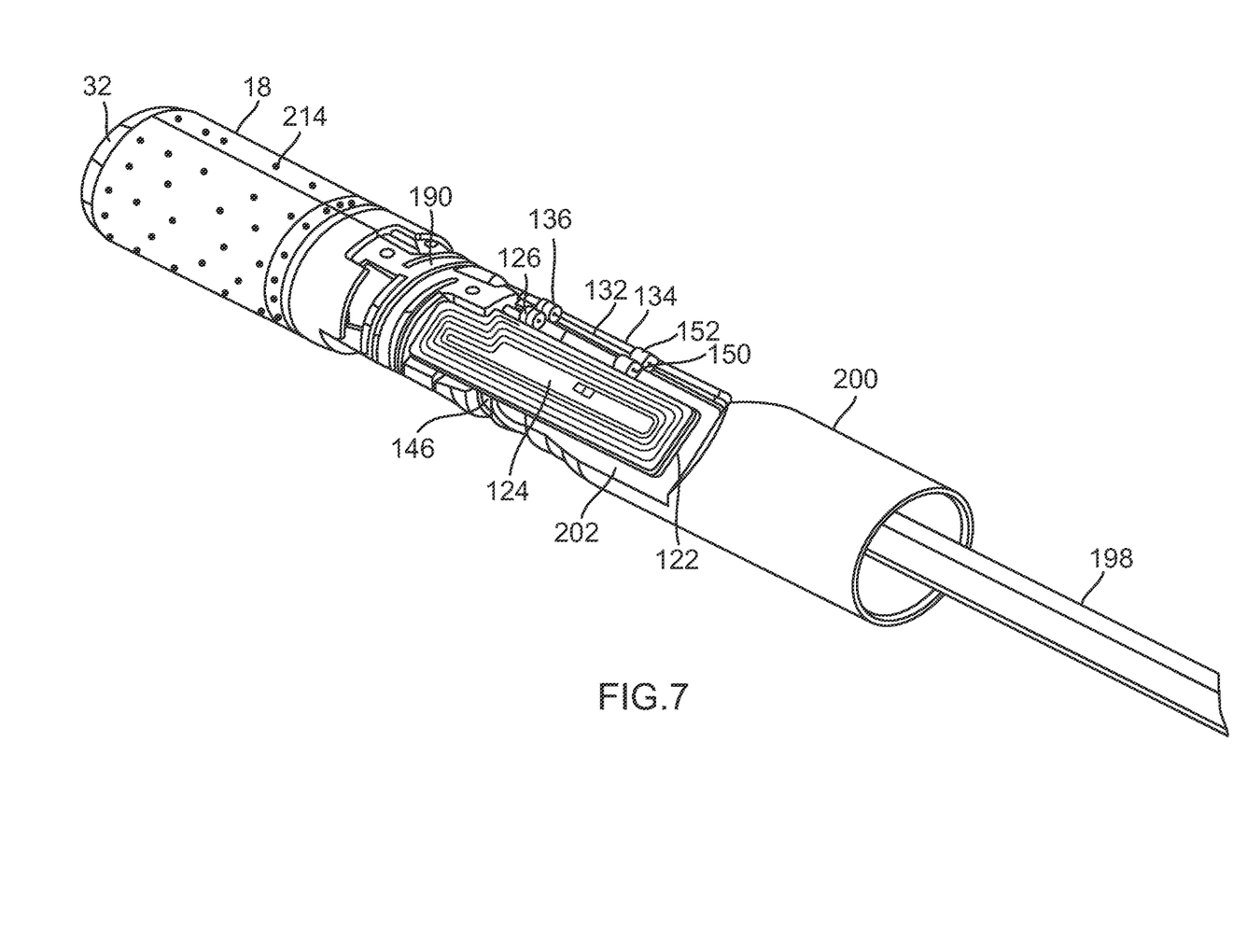
FIG. 7 depicts the distal portion of the catheter of FIG. 1 in a further partially assembled configuration.
Figure 8:
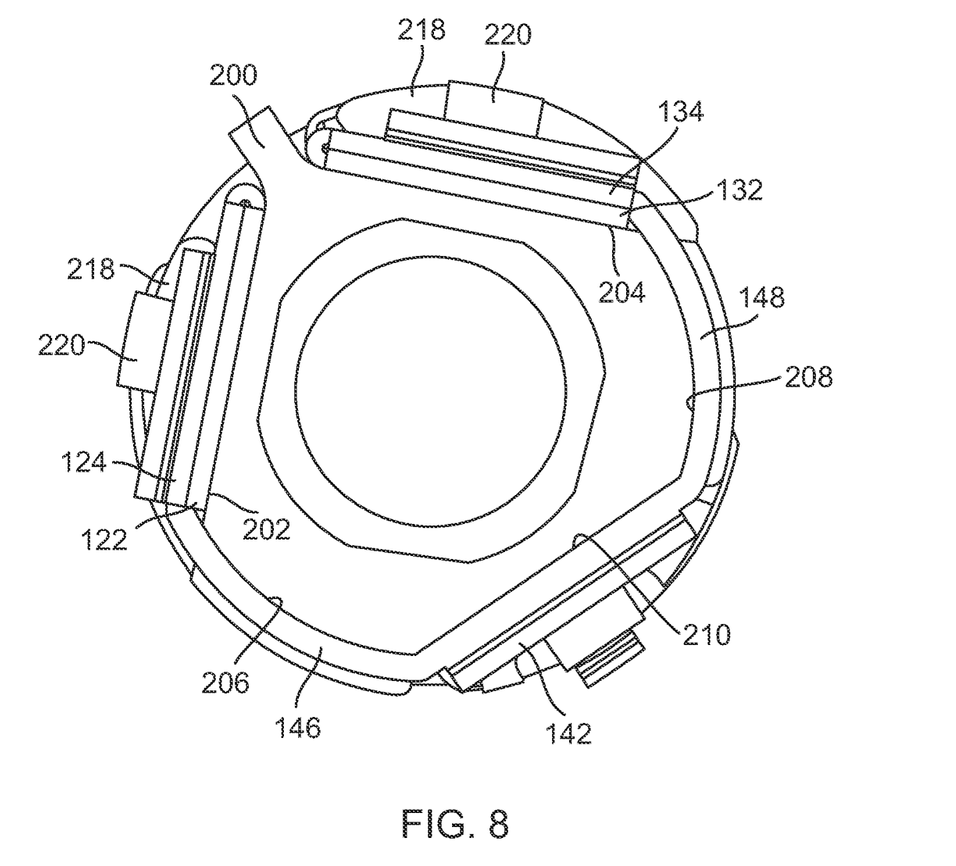
FIG. 8 depicts a cross section taken through line A-A of FIG. 6.

FIGS. 6 and 7 show catheter 14 at two different steps of its assembly. FIG. 8 is a cross section of catheter 14 taken along line A-A in FIG. 6, but with various components removed or simplified for clarity concerning further discussion of flexible circuit 110. FIG. 6 shows flexible circuit 110 as assembled to spring 190 and a coupling sleeve 200. Although not seen, first portion 114 of flexible circuit 110 is adhered to top face 192 of spring 190 and flexible circuit 180 is adhered to bottom face 194 of spring 190. In FIG. 7, tip 18, which itself may be include ablation electrode(s) 32, and which includes various irrigation apertures 214, is attached to spring 190. Also shown in FIGS. 6 and 7 is cable bundle 198. Cable bundle 198 includes a set of cables, which, although not visible, are connected to solder joints 168 on fourth portion 142 of flexible circuit 110, and thus to the various coils or traces on flexible circuit 110, and to coils or traces 184 on flexible circuit 180. As seen in FIGS. 6-8, flexible circuit 110 is no longer planar. Rather, it has been deformed to have a shape that has a cross section that is partially circular and partially triangular. Segment 124 of second portion 116 is the most readily visible segment of flexible circuit 110 in FIGS. 6 and 7. Various sides of segment 122, segment 132, and segment 134, as well as connectors 126, 136, 146, 150, and 152 are also visible in these figures. As seen these connectors have been deformed into bent or curved configurations for attachment to coupling sleeve 200. Specifically, segment 122 is adhered to a substantially planar surface 202 of sleeve 200 and segment 132 is adhered to a substantially planar surface 204 of sleeve 204. So assembled, these portions of flexible circuit 110 may be viewed as having a triangular cross section. Further, connector 146 is adhered to a circular (or arcuate) surface 206 of sleeve 200 and connector 148 is adhered to a circular (or arcuate) surface 208 of sleeve 200. So assembled, these portions of flexible circuit 110 may be viewed as having a circular (or arcuate) cross section. Fourth portion 142 may further be adhered to substantially planar surface 210 of sleeve 200.

The diameter or width of the circular portion of the cross section of flexible circuit 110 as assembled to sleeve 200 is equal or approximately equal to the diameter or maximum width of first portion 114, which is also equal or approximately equal to the maximum width (or base) of the triangular portion of the cross-section of flexible circuit 110 as assembled to sleeve 100. Accordingly, as assembled, flexible circuit 110, may be readily inserted into an outer tube or sleeve 216 (FIG. 1) that provides an outer surface of catheter 14 and that defines the inner diameter within which componentry (e.g., flexible circuit 110, spring 180, sleeve 200) of catheter 14 must fit. To help prevent soft spots under sleeve 216 that result from gaps between the substantially planar outer surfaces of segments 124 and 134, and portion 142 on the one hand, and the curvature of sleeve 216 on the other hand, these gaps may be filled by including additional material, e.g., adhesives 218 and polyimide layers 220, on segments 124 and 134 (of second portion 116 and third portion 130, respectively) and portion 142. The polyimide layers 220 may be fabricated separately from flexible circuit 110 and adhered thereto, or they may be an integral portion of flexible circuit 110, formed during the same lithographic process as the remainder of flexible circuit 110. Polyimide layers 220 may interpolate the curve of sleeve 216 with a series of substantially planar steps or layers.

Flexible circuit 110 may be assembled into catheter 14 as follows. First, flexible circuit 110 may be provided. Segment 124 of second portion 116 may be folded over segment 122 of second portion 116 to overlap it and contact it by deforming connector 126 and, if included, connector 150. Segment 134 of third portion 130 may be folded over segment 132 of third portion 130 to overlap it and contact it by deforming connector 136 and, if included, connector 152. First portion 114 of flexible circuit 110 may be oriented to be parallel to top face 192 of spring 190, which is oriented transversely (e.g., less than thirty degrees from perpendicular) to a longitudinal axis of spring 190. First portion 114 may then be adhered to top face 192 of spring 190. A coupling sleeve 200 having substantially planar surface portions may be provided and oriented to align its longitudinal axis with the longitudinal axis of the spring. Second portion 116 and third portion 130 may be oriented to be parallel to respective substantially planar surface portions of sleeve 200. Then, second portion 116 and third portion 130 may be adhered to the respective substantially planar surface portions of sleeve 200. Sleeve 200, adhered to flexible circuit 110, may then be coupled or inserted into outer sleeve 216. Finally, tip 18 may be affixed to spring 190. Flexible circuit 180 may be adhered to bottom face 194 of spring 190 at nearly any step of the process so long as tip 18 has not been attached to spring 190.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A flexible circuit, comprising:
    a substrate fabricated via a lithographic process such that the substrate comprises between a first number of layers and a second number of layers, the substrate including a first portion and a second portion;
    the first portion comprising a first first-portion segment and a second first-portion segment, the first first-portion segment having a first shape and the second first-portion segment having a second shape that is a mirror image of the first shape; and
    the second portion comprising a first second-portion segment and a second second-portion segment, the first second-portion segment having a third shape and the second second-portion segment having a fourth shape that is a mirror image of the third shape,
    in which the first first-portion segment, the second first-portion segment, the first second-portion segment, and the second second-portion segment are comprised from the same layers of the substrate.

2. The flexible circuit of claim 1, in which the first shape and the fourth shape are a same shape.

3. The flexible circuit of claim 1, in which the first portion has a first-portion shape and the second portion has a second-portion shape that is a mirror image of the first-portion shape.

4. The flexible circuit of claim 3, in which a midline bisects the planar substrate such that the first portion is disposed to a first side of the midline and the second portion is disposed to a second side of the midline.

5. The flexible circuit of claim 4, in which the first portion further comprises a first first-portion connector that connects the first first-portion segment to the second first-portion segment and the second portion further comprises a first second-portion connector that connects the first second-portion segment to the second second-portion segment.

6. The flexible circuit of claim 5, in which the first portion further comprises a second first-portion connector that connects the first first-portion segment to the second first-portion segment and the second portion further comprises a second second-portion connector that connects the first second-portion segment to the second second-portion segment.

7. The flexible circuit of claim 6, in which the first first-portion segment comprises a first coil and the second first-portion segment comprises a second coil that is a mirror image of the first coil.

8. The flexible circuit of claim 7, in which the substrate further comprises a third portion that is bisected by the midline, the third portion being disposed between the first portion and the second portion.

9. The flexible circuit of claim 8, in which the third portion comprises a plurality of solder joints and the first coil is connected to a first solder joint of the plurality of solder joints via a first coil extension and the second coil is connected to a second solder joint of the plurality of solder joints via a second coil extension.

10. The flexible circuit of claim 9, in which the first second-portion segment comprises a third coil and the second second-portion segment comprises a fourth coil that is a mirror image of the third coil.

11. The flexible circuit of claim 10, in which the third coil is connected to a third solder joint of the plurality of solder joints via a third coil extension and the fourth coil is connected to a fourth solder joint of the plurality of solder joints via a fourth coil extension.

12. The flexible circuit of claim 11, further comprising a first third-portion connector that connects the first portion to the third portion and a second third-portion connector that connects the second portion to the third portion.

13. The flexible circuit of claim 7, in which the first first-portion segment is disposed atop the second first-portion segment and the first second-portion segment is disposed atop the second second-portion segment.

14. The flexible circuit of claim 10, in which the first coil is aligned with the second coil and the third coil is aligned with the fourth coil.

* * * * *